US012533204B2

(12) United States Patent
Hibner et al.

(10) Patent No.: US 12,533,204 B2
(45) Date of Patent: Jan. 27, 2026

(54) CIRCULARITY SYSTEMS AND METHODS FOR HARMONIC VESSEL SEALERS

(71) Applicant: Cilag GmbH International, Zug (CH)

(72) Inventors: John A. Hibner, Mason, OH (US); David Monroe, Cincinnati, OH (US); Thomas B. Remm, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 300 days.

(21) Appl. No.: 18/350,241

(22) Filed: Jul. 11, 2023

(65) Prior Publication Data

US 2025/0017680 A1 Jan. 16, 2025

(51) Int. Cl.

*A61B 17/32* (2006.01)
*A61B 34/30* (2016.01)
*A61B 90/00* (2016.01)

(52) U.S. Cl.

CPC .............. *A61B 90/08* (2016.02); *A61B 34/30* (2016.02); *A61B 2034/305* (2016.02)

(58) Field of Classification Search

CPC .... A61B 17/320068; A61B 17/320092; A61B 2017/00455; A61B 2017/00477; A61B 2017/2929; A61B 2017/2933; A61B 2017/2945; A61B 2017/320071; A61B 2017/320094

See application file for complete search history.

(56) References Cited

U.S. PATENT DOCUMENTS

2019/0059933 A1 * 2/2019 Miller ............ A61B 17/320068

* cited by examiner

*Primary Examiner* — Jon Eric C Morales

(74) *Attorney, Agent, or Firm* — Vorys, Sater, Seymour and Pease LLP

(57) ABSTRACT

A method of replacing a surgical tool consumable, the surgical tool including a drive housing containing an ultrasonic transducer, a shaft extending distally from the drive housing, an end effector coupled to the shaft and including a blade operatively coupled to the ultrasonic transducer and extending from drive housing within the shaft, and a clamp assembly that includes a clevis extending about the blade and a clamp arm pivotably coupled to the clevis such that axial movement of the clevis causes the clamp arm to move between open and closed positions, and a wrist interposing the shaft and the end effector. The method further including decoupling the blade from the ultrasonic transducer, removing the end effector from the wrist and proximal portions of the surgical tool, replacing the consumable of the surgical tool, and reconnecting the end effector to the wrist and the proximal portions of the surgical tool.

19 Claims, 10 Drawing Sheets

CIRCULARITY SYSTEMS AND METHODS FOR HARMONIC VESSEL SEALERS

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have been developed to assist in MIS procedures. Robotic systems can allow for more instinctive hand movements by maintaining natural eye-hand axis. Robotic systems can also allow for more degrees of freedom in movement by including an articulable “wrist” joint that creates a more natural hand-like articulation. In such systems, an end effector positioned at the distal end of the instrument can be articulated (moved) using a cable driven motion system having one or more drive members that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system. Moving the drive members articulates the end effector to desired angular positions and configurations. Some MIS instruments, however, do not have a cable driven motion system, but instead include other features or mechanisms that facilitate articulation and operation.

MIS instruments incorporate various high-wear components that, over time, can mechanically or physically degrade and thereby limit the useful life of the instrument. Consequently, most MIS instruments are designed to be used only for a predetermined number of procedures, following which the instrument is often discarded. As can be appreciated, this can have an adverse impact on the environment.

In an effort to maintain the value of products, while simultaneously not creating additional environmental waste, companies and manufacturers are progressively looking for ways to incorporate “circularity” into their business model. Circularity is an economic model that follows the three “Rs”: reuse, reprocess, and recycle, and aims to retain the lifespan of products through repair and maintenance, reusing, remanufacturing, or upcycling.

What is needed is a process or methodology of circularity concerning the reuse and recycling of MIS instruments, which minimizes the impact on the environment.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to surgical tools and, more particularly, to prolonging the lifespan of surgical tools by implementing circularity systems and methods that result in replacement of one or more consumables included in the surgical tool.

The utilization or “lifespan” of a majority of robotic (and non-robotic) surgical tools is often limited due to the life or durability of just a few components within the surgical tool, referred to herein as “consumables”. Embodiments disclosed herein describe how the design of the surgical tool can be modified to enable the consumable to be replaced rather easily, without requiring the surgical tool to be completely disassembled. Accordingly, the embodiments disclosed herein may prove advantageous in mitigating or entirely eliminating the need to scrap an entire surgical tool, but instead rehabilitate the used surgical tool by replacing one or more consumables.

Figure 1:
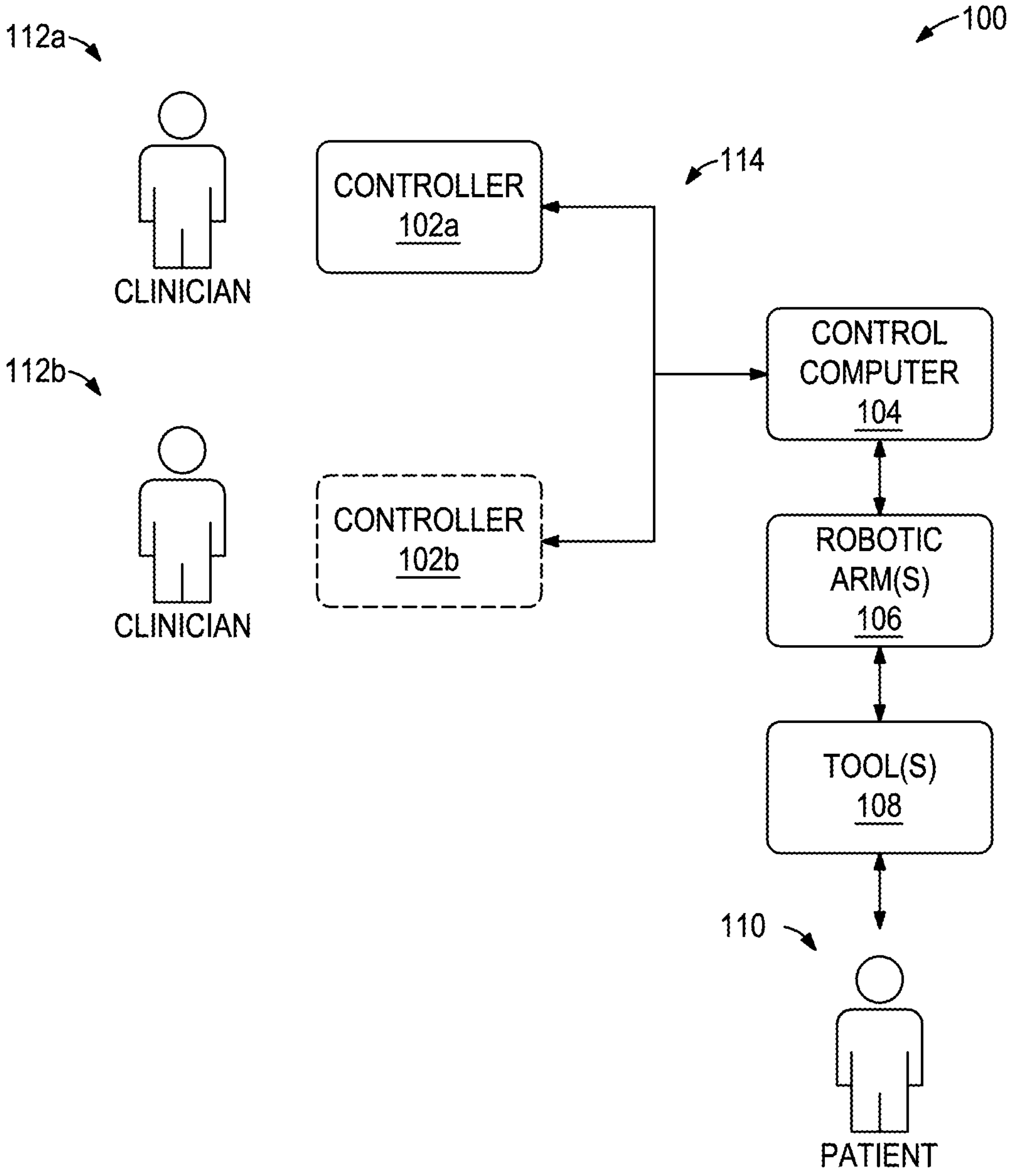
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102*a* and at least one control computer 104. The control computer 104 may be mechanically and/or electrically coupled to a robotic manipulator and, more particularly, to one or more robotic arms 106 (alternately referred to as “tool drivers”). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112*a* (e.g., a surgeon) from the user input controller 102*a*.

In some embodiments, a second set of user input controllers 102*b* (shown in dashed line) may be operated by a second clinician 112*b* to direct operation of the robotic arms 106 and tools 108 via the control computer 104 and in conjunction with the first clinician 112*a*. In such embodiments, for example, each clinician 112*a,b* may control different robotic arms 106 or, in some cases, complete control of the robotic arms 106 may be passed between the clinicians 112*a,b* as needed. In some embodiments, additional robotic manipulators having additional robotic arms may be utilized during surgery on the patient 110, and these additional robotic arms may be controlled by one or more of the user input controllers 102*a,b*.

The control computer 104 and the user input controllers 102*a,b* may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102*a,b* generally include one or more physical controllers that can be grasped by the clinicians 112*a,b* and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112*a,b* via a display to provide a visual indication of various surgical instrument metrics, such as the amount of force being applied to the surgical instrument (i.e., a cutting instrument or dynamic clamping member).

Figures 2, 3:
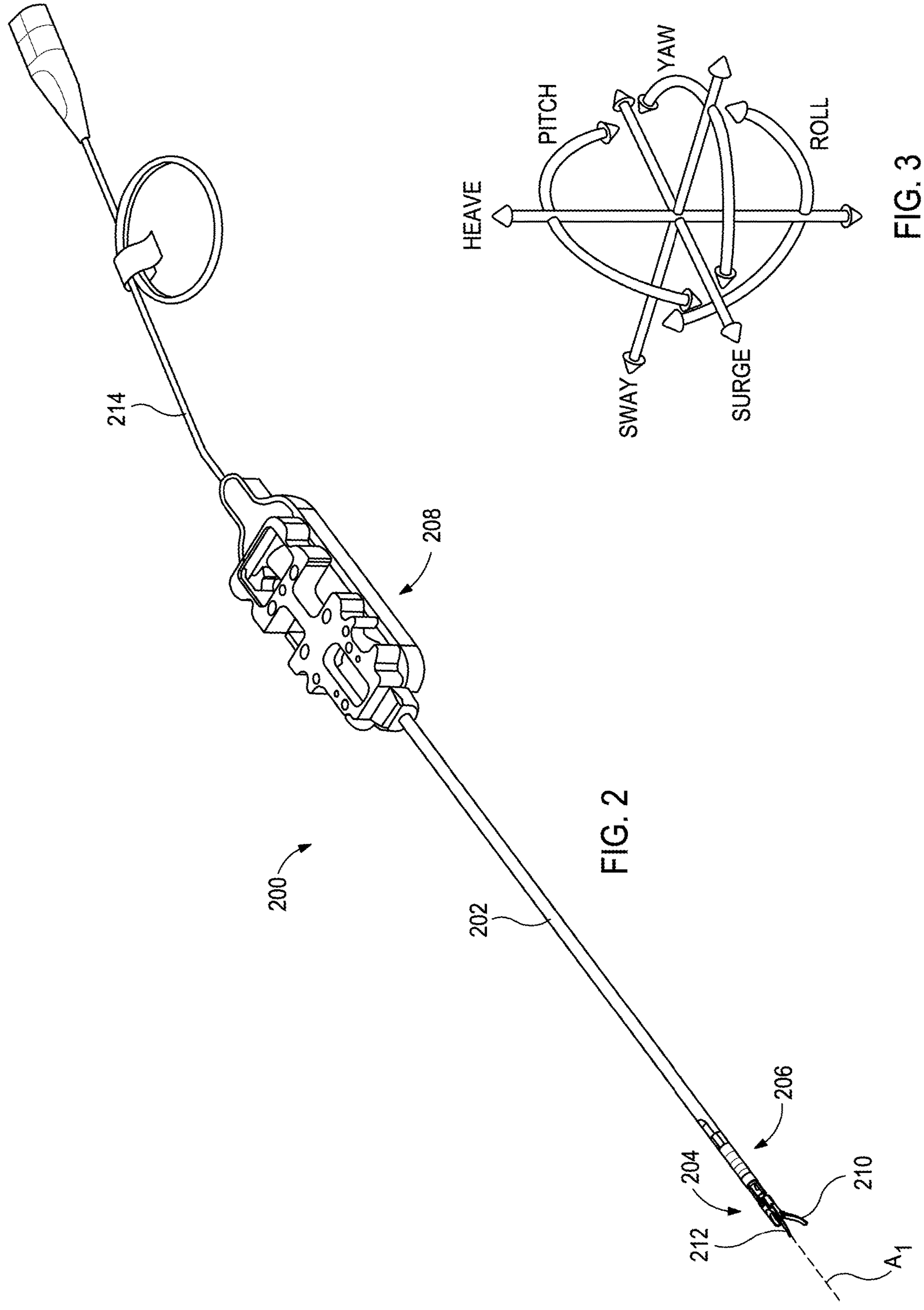
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) and translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the drive housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the drive housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the drive housing 208 is configured to control rotational movement of the shaft 202 about the longitudinal axis $A_1$.

The shaft 202 is an elongate member extending distally from the drive housing 208 and has at least one lumen extending therethrough along its axial length. In some embodiments, the shaft 202 may be fixed to the drive housing 208, but could alternatively be rotatably mounted to the drive housing 208 to allow the shaft 202 to rotate about the longitudinal axis $A_1$. In yet other embodiments, the shaft 202 may be releasably coupled to the drive housing 208, which may allow a single housing 208 to be adaptable to various shafts having different end effectors.

The end effector 204 can exhibit a variety of sizes, shapes, and configurations. In the illustrated embodiment, the end effector 204 comprises a harmonic vessel sealer, also referred to as "harmonic shears" or a "harmonic dissector," that includes a pivotable jaw or "clamp arm" 210 and a blade 212. The pivotable clamp arm 210 is configured to pivot relative to the blade 212 between open and closed positions, and the blade 212 is operable to transfer and/or amplify ultrasonic energy from an ultrasonic transducer housed within the drive housing 208 into tissue to simultaneously cut and seal tissue grasped between the blade 212 and the clamp arm 210. In other applications, the end effector 204 may comprise other types of tools with opposing jaws such as, but not limited to, a surgical scissors, a clip applier, a tissue grasper, a vessel sealer, a combination tissue grasper and vessel sealer, a needle driver, a babcock including a pair of opposed grasping jaws, bipolar jaws (e.g., bipolar Maryland grasper, forceps, a fenestrated grasper, etc.), etc.

FIG. 3 illustrates the potential degrees of freedom in which the wrist 206 may be able to articulate (pivot) and thereby move the end effector 204. The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of the end effector 204 with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive members (obscured in FIG. 2) that form part of an actuation system configured to facilitate actuation and articulation of the end effector 204 relative to the shaft 202. Moving (actuating) one or more of the drive members moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the drive housing 208. In other embodiments, the power cable 214 may be omitted and electrical power may be supplied to the surgical tool 200 via an internal power source, such as one or more batteries, capacitors, or fuel cells. In such embodiments, the surgical tool 200 may alternatively be characterized and otherwise referred to as an "electrosurgical instrument" capable of providing electrical energy to the end effector 204.

The power cable 214 may place the surgical tool 200 in electrical communication with a generator that supplies energy, such as electrical energy (e.g., radio frequency energy), ultrasonic energy, microwave energy, heat energy, or any combination thereof, to the surgical tool 200 and, more particularly, to the end effector 204. Accordingly, the generator may comprise a radio frequency (RF) source, an ultrasonic source, a direct current source, and/or any other suitable type of electrical energy source that may be activated independently or simultaneously.

Similar to most surgical tools, the surgical tool 200 includes various high-wear components referred to herein as "consumables" that, over time, can mechanically or physically degrade and thereby limit the useful life of the surgical tool 200. Consequently, the surgical tool 200 may be designed to be used for only a predetermined number of procedures. Once the predetermined number of procedures is reached, the operator (e.g., a nurse, a doctor, etc.) may be unable to continue using the surgical tool 200. In such cases, the surgical tool 200 would conventionally be discarded, which can have an adverse impact on the environment.

According to embodiments of the present disclosure, instead of discarding the surgical tool 200, the surgical tool 200 may be subject to circularity processing or a circular economy model or approach designed to reprocess and recycle the surgical tool 200 for further use. In circularity processing, the surgical tool 200 is decommissioned upon reaching the predetermined number of procedures, and then subsequently sent to a service center where trained technicians clean and mount the surgical tool 200 to a disassembly fixture. While mounted to the disassembly fixture, various portions of the surgical tool 200 may be disassembled to access and remove one or more consumables forming part of the surgical tool 200. The removed consumables can then be cleaned and refurbished or replaced with new consumables. The surgical tool 200 may then be reassembled, cleaned, tested, delivered to a distribution center, and subsequently sent to an end user (e.g., a hospital, a surgeon, an operator, etc.) for further use.

Figure 4:
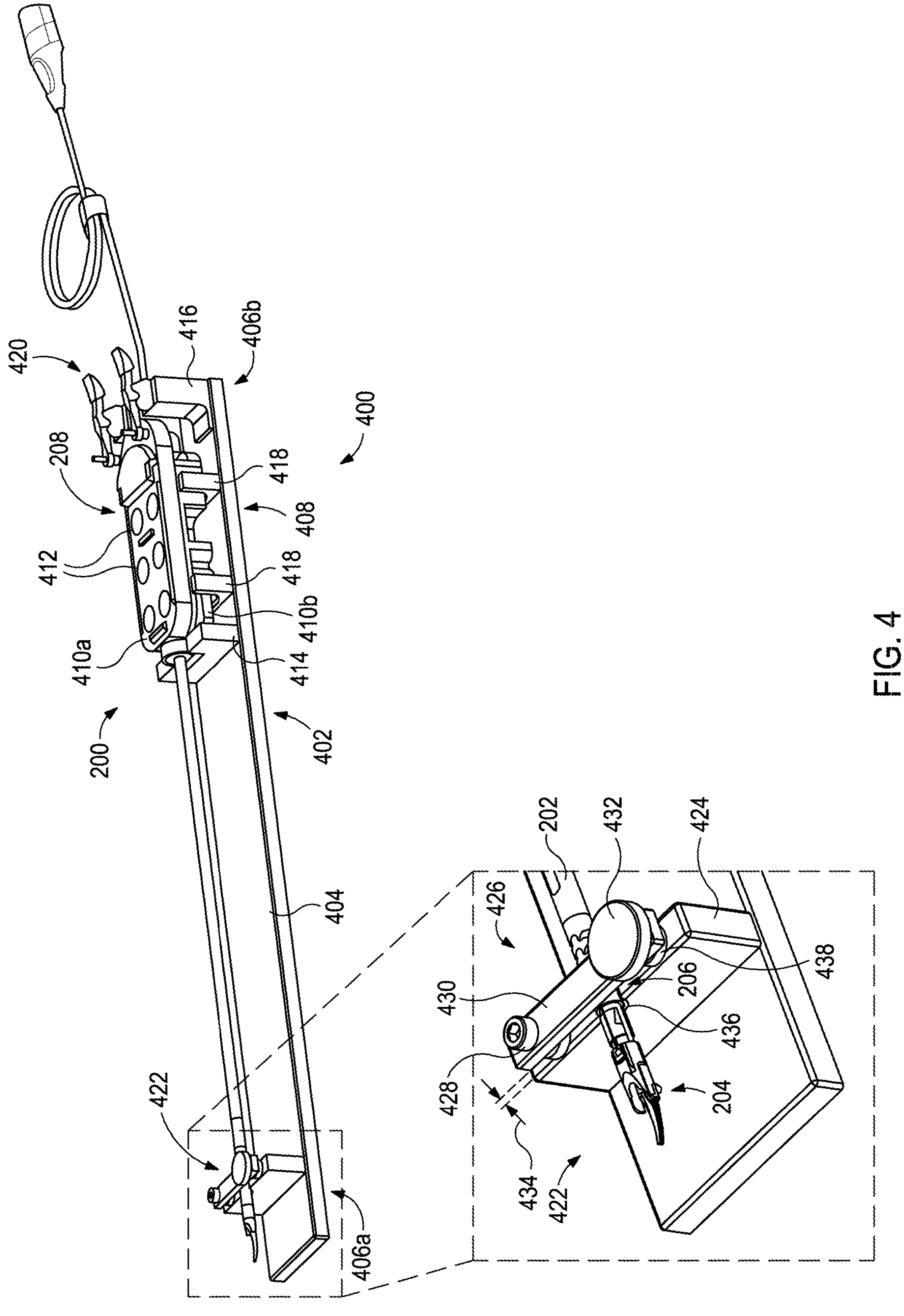
FIG. 4 is an isometric side view of an example circularity processing system, according to one or more embodiments.

FIG. 4 is an isometric side view of an example surgical tool circularity processing system 400, according to one or more embodiments. As illustrated, the surgical tool circularity processing system 400 includes a disassembly fixture 402 configured to receive and mount the surgical tool 200. The disassembly fixture 402 may be provided at a service center that employs technicians trained to clean, disassemble, and refurbish the surgical tool 200, as described herein.

As illustrated, the disassembly fixture 402 provides an elongate base 404 having a first or "distal" end 406*a* and a second or "proximal" end 406*b* opposite the distal end 406*a*. In some embodiments, as illustrated, the base 404 may exhibit a generally rectangular shape, but could alternatively exhibit other shapes without departing from the scope of the disclosure.

A drive housing mount 408 may be provided at the proximal end 406*b* and configured to receive and seat the drive housing 208, which may include a bottom portion 410*a* matable with a top portion 410*b*. In the illustrated embodiment, the drive housing 208 is shown received within the drive housing mount 408 such that the bottom portion 410*a* faces upwards and is otherwise exposed. In such embodiments, some or all of the bottom portion 410*a* may be removed by the technician to access various internal components of the drive housing 208, as described in more detail below. In other embodiments, or in addition thereto, a robotic manipulator (not shown) may be attached to the bottom portion 410*a* to manipulate and operate one or more drive inputs 412 rotatably mounted to the bottom of the drive housing 208. In other embodiments, however, the drive housing 208 may be received within the drive housing mount 408 with the top portion 410*b* facing upwards, without departing from the scope of the disclosure.

As illustrated, the drive housing mount 408 may include a plurality of structural elements extending from or otherwise forming part of the body 404 and designed to receive and seat the drive housing 208. More particularly, the drive housing mount 408 may include a cradle or "yoke" 414, a rear support 416, and one or more side supports 418 (two visible) provided at various locations between the yoke 414 and the rear support 416. The yoke 414 may be configured to support the distal end of the drive housing 208, and the rear support 416 may be configured to support the proximal end of the drive housing 208. The side supports 418 may be configured to support the lateral sides of the drive housing 208.

In some embodiments, the drive housing mount 408 may further include one or more clamps 420 (two shown) operable to secure the drive housing 208 to the base 404 when properly received within the drive housing mount 408. In some embodiments, as illustrated, the clamp(s) 420 may be mounted to the rear support 416, but could alternatively be mounted to other portions of the drive housing mount 408 or the base 404, without departing from the scope of the disclosure.

A vice, referred to herein as an "end effector mount" 422, may be provided and otherwise defined at or near the distal end 406*a* of the base 404 and configured to receive and seat the distal end of the surgical tool 200. More specifically, and as shown in the enlarged, inset graphic, the end effector mount 422 may include a bracket or stand 424 and a securing clasp or mechanism 426 may be pivotably attached to the stand 424. The securing mechanism 426 may include a pivot joint 428, a securing bar 430 extending from the pivot joint 428, and a mechanical fastener 432 arranged at the end of the securing bar 430 opposite the pivot joint 428. As mounted to the pivot joint 428, the securing bar 430 may be vertically offset a short distance from the stand 424, such that a gap 434 is provided between the securing bar 430 and the top of the stand 424. The gap 434 may be large enough to receive the distal end of the surgical tool 200 when the securing mechanism 426 is secured to the stand 424.

To secure the distal end of the surgical tool 200 to the disassembly fixture 402 and, more particularly, to the end effector mount 422, the distal end of the surgical tool 200 is first placed atop the stand 424 such that the shaft 202 or portions of the wrist 206 engage the top of the stand 424. In some embodiments, as illustrated, the top of the stand 424 may define and otherwise provide an arcuate groove 436 sized to receive and seat the distal end of the surgical tool 200; e.g., the wrist 206 and/or the end effector 204. The securing bar 430 may then be pivoted about the pivot joint 428 until the mechanical fastener 432 is able to locate and mate with a corresponding securing receptor 438. Operating or otherwise securing the mechanical fastener 432 to the securing receptor 438 may place a load on the distal end of the surgical tool 200, which helps prevent the surgical tool 200 from moving up or down, or translating axially. In the illustrated embodiment, the mechanical fastener 432 comprises a thumbscrew, but could alternatively comprise other types of mechanical fasteners or fastening means suitable for securing the securing bar 430 to the stand 424 and thereby helping to secure the surgical tool 200 to the disassembly fixture 402.

Those skilled in the art will readily appreciate that the end effector mount 422 including the securing mechanism 426 is merely one example embodiment consistent with the principles of the present disclosure. Indeed, other means and configurations of the end effector mount 422 and/or the securing mechanism 426 are possible and contemplated herein, without departing from the scope of the disclosure.

Figure 5A:
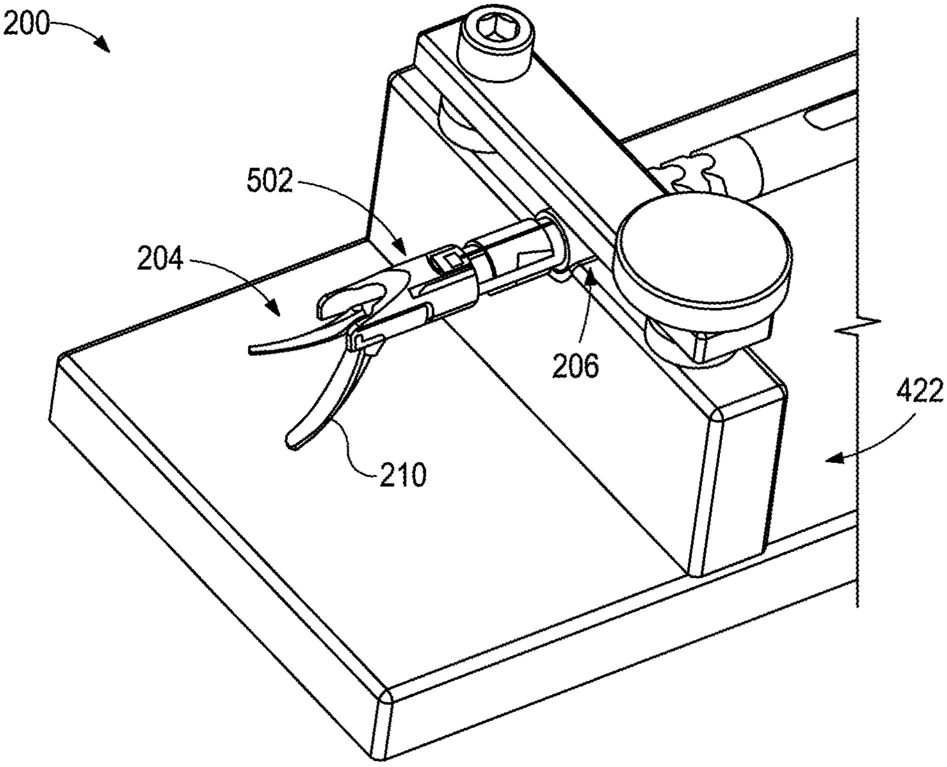
FIGS. 5A and 5B are enlarged isometric view of the distal end of the surgical tool of FIG. 2 as mounted to the end effector mount of FIG. 4.
Figure 5B:
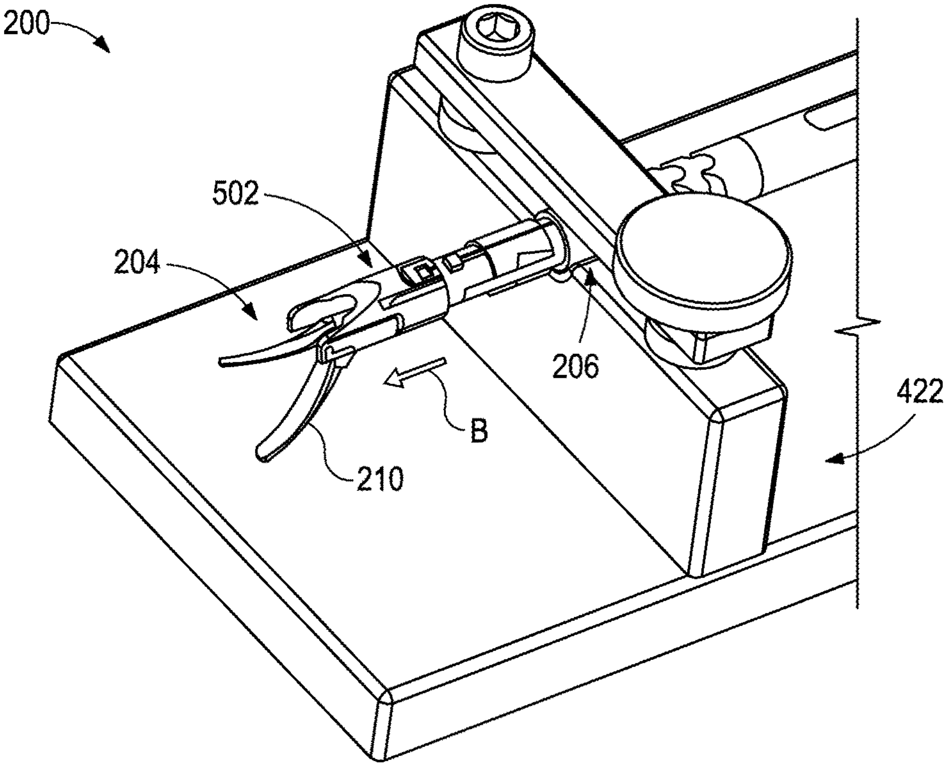

FIGS. 5A and 5B are enlarged isometric views of the distal end of the surgical tool 200 mounted (secured) to the end effector mount 422, according to one or more embodiments. Once the distal end of the surgical tool 200 is properly mounted to the end effector mount 422, the clamp arm 210 may be pivoted to the fully open position, as shown in FIGS. 5A-5B. In some embodiments, this can be accomplished by manually moving (rotating) the drive input 412 (FIG. 4) associated with actuation (movement) of the clamp arm 210. In other embodiments, however, a robotic manipulator may be secured to the bottom portion 410*a* (FIG. 4) of the drive housing 208 (FIG. 4) and operated to actuate the drive input 412 associated with actuation (movement) of the clamp arm 210.

As illustrated, the end effector 204 may include a clevis 502 that forms part of a clamp assembly that is actuatable to move the clamp arm 210 between the open and closed positions. To be able to access one or more "consumables" included in the surgical tool 200, the clamp assembly must first be disassembled from proximal portions of the surgical tool 200 and, more specifically, the end effector 204 must be separated from the wrist 206. To accomplish this, the clevis 502 must first be disconnected from proximal portions of the surgical tool 200 and moved distally and away from the proximal portions. In FIG. 5A, the clevis 502 is shown in a first or "attached" position as operatively coupled to the proximal portions of the surgical tool 200, and in FIG. 5B, the clevis 502 detached from the proximal portions and moved distally to a second or "released" position, as shown by the arrow B.

Figure 6A:
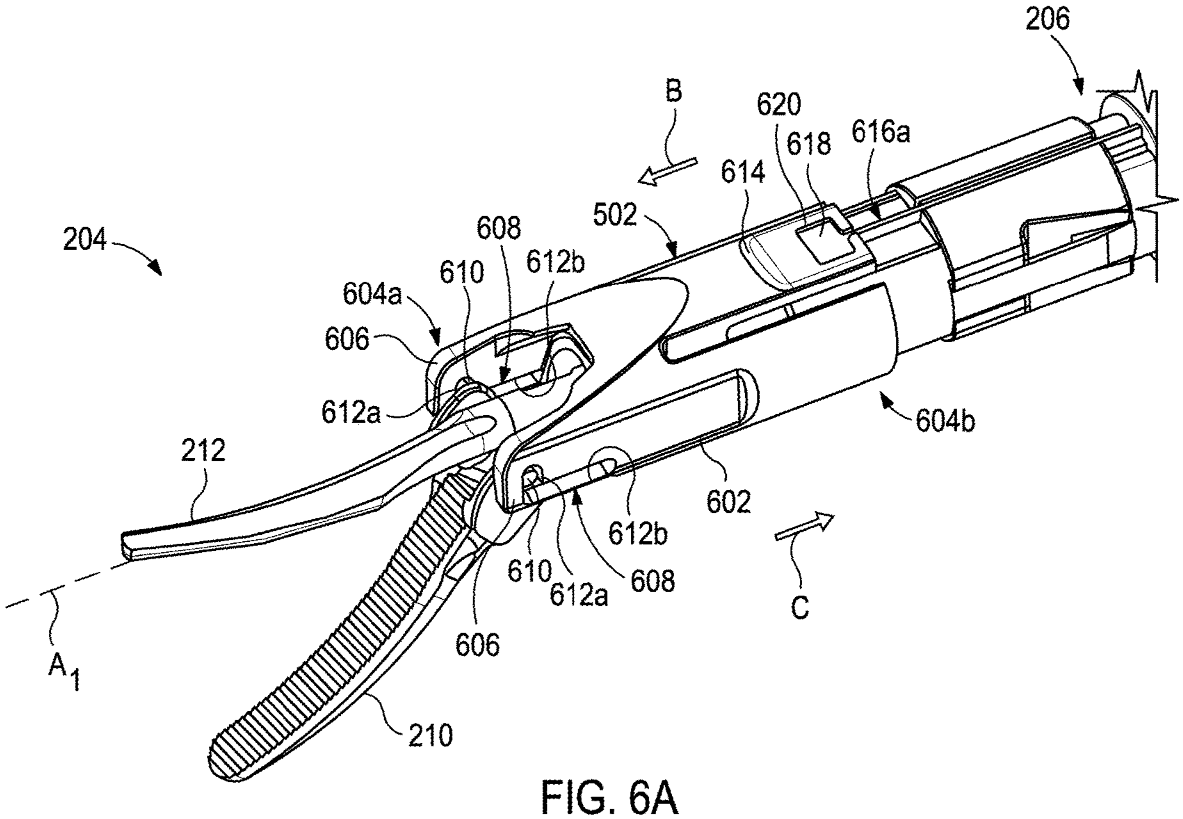
FIG. 6A is an isometric view of the end effector, according to one or more embodiments.

Referring to FIG. 6A, illustrated is an isometric side view of the end effector 204, according to one or more embodiments. The clevis 502 is mounted to and otherwise forms part of the end effector 204. As illustrated, the clevis 502 provides a generally cylindrical body 602 having a first or "distal" end 604*a* and a second or "proximal" end 604*b* opposite the distal end 604*a*. At the distal end 604*a*, the body 602 provides or otherwise defines first and second distally extending arms 606 angularly offset from each other on opposing sides of the body 602. A gap is defined laterally between the distally extending arms 606 to accommodate the blade 212 and the clamp arm 210 therebetween.

The clamp arm 210 may be pivotably mounted to the distally extending arms 606. More specifically, each distally extending arm 606 defines a slot or "pivot channel" 608, and the clamp arm 210 defines laterally extending clamp pins 610 extending from opposing sides of the clamp arm 210 and positioned to be received within the laterally adjacent pivot channel 608. Moreover, each pivot channel 608 includes a vertical slot 612*a* and a horizontal slot 612*b* that is contiguous with and extends proximally from the vertical slot 612*a*. In some embodiments, the horizontal slot 612*b* extends substantially parallel with the longitudinal axis $A_1$ of the shaft 202, and the vertical slot 612*a* extends substantially perpendicular thereto. In such embodiments, the pivot channel 608 may be generally characterized as an "L-shaped" channel. In other embodiments, however, the vertical slot 612*a* can extend from the horizontal slot 612*b* at an angle offset from perpendicular, without departing from the scope of the disclosure.

At the proximal end 604*b*, the body 602 provides and otherwise defines first and second proximally extending tabs 614 (one visible in FIG. 6A). The first and second tabs 614 are angularly offset from each other by 180° and may be configured to be operatively coupled to first and second drive members 616*a* and 616*b* (the drive member 616*b* is occluded in FIG. 6A, see FIGS. 6B and 6C). The drive members 616*a,b*, alternately referred to as "jaw closure bands," extend from the drive housing 208 (FIGS. 2 and 4) on angularly opposite sides of the shaft 202 (FIGS. 2 and 4) and through the wrist 206. The drive members 616*a,b* form part of the actuation system housed within the drive housing 208, and may comprise bands, elongate members, belts, shafts, flexible shafts, drive rods, or any combination thereof. The drive members 616*a,b* can be made from a variety of materials including, but not limited to, a metal (e.g., tungsten, stainless steel, nitinol, etc.), a polymer (e.g., ultra-high molecular weight polyethylene), a synthetic fiber (e.g., KEVLAR®, VECTRAN®, etc.), an elastomer, or any combination thereof.

In the drive housing 208 (FIGS. 2 and 4), the drive members 616*a,b* are operatively coupled to actuation mechanisms or devices that facilitate longitudinal movement (translation) of the drive members 616*a,b*. Selective actuation of the drive members 616*a,b* at the drive housing 208 applies push and pull forces on the drive members 616*a,b*, which urges the drive members 616*a,b* to translate longitudinally in distal or proximal directions, which correspondingly moves the clevis 502 in the same direction. More specifically, each drive member 616*a,b* provides or defines a coupling head 618 sized to be received within a corresponding head aperture 620 defined in an adjacent proximally extending tab 614. Receiving the coupling head 618 in the corresponding head aperture 620 operatively couples the associated drive member 616*a,b* to the clevis 502 such that longitudinal movement of the drive member 616*a,b* correspondingly moves the clevis 502 in the same longitudinal direction; e.g., distally or proximally.

Figure 6B:
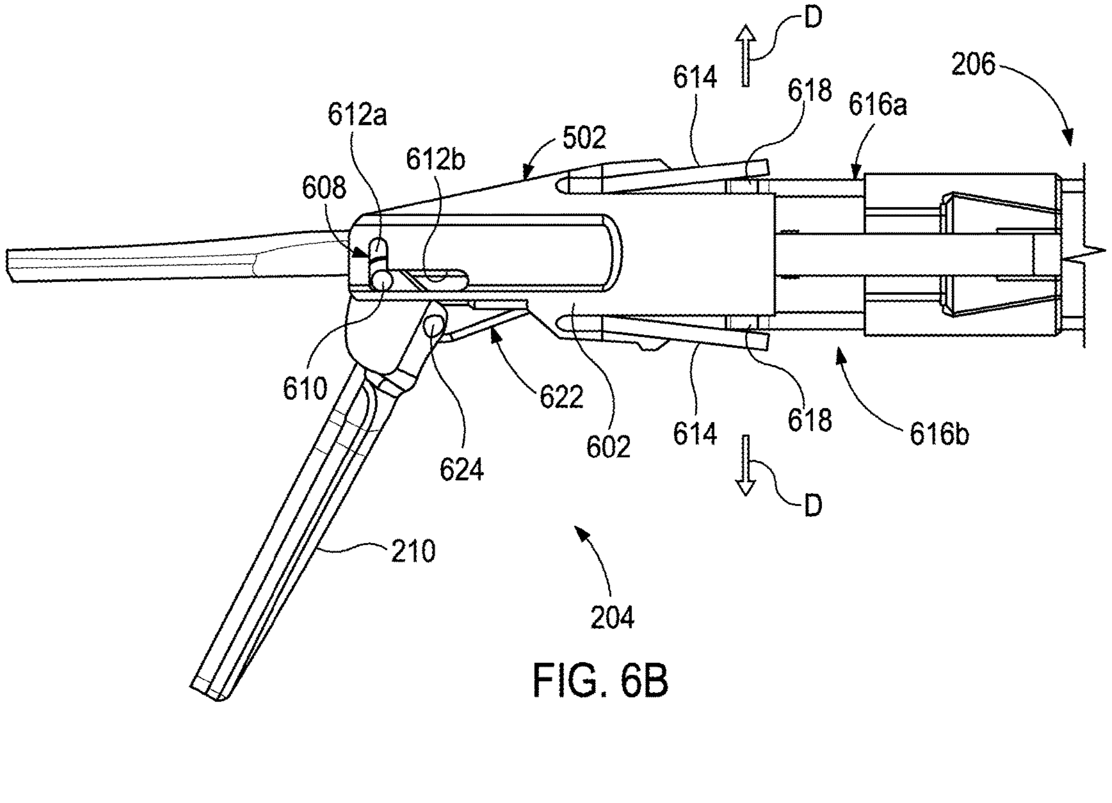
FIGS. 6B and 6C are schematic side views of the end effector showing example disassembly of the clevis, according to one or more embodiments.

Referring to FIG. 6B with continued reference to FIG. 6A, to actuate the clamp arm 210 between the open and closed positions, the drive members 616*a,b* are simultaneously moved in the same longitudinal direction (either distally or proximally), which correspondingly moves the clevis 502 in the same longitudinal direction. The clamp arm 210 may be pivotably attached to a pivot base 622 interposing the blade 212 and the clevis 502 and forming part of the clamp assembly. The clamp arm 210, the clevis 502, and the pivot base 622 may be combined and cooperatively referred to herein as "the clamp assembly".

The clamp arm 210 may be pivotably attached to the pivot base 622 at a pivot pin 624, and the clamp arm 210 is opened by urging the clevis 502 to move (translate) in the distal direction B (FIG. 6A). As the clevis 502 moves distally, the pins 610 will be forced against the vertical slot 612*a*, which transfers the load to the pivot pin 624 and thereby urges the clamp arm 210 to pivot relative to the pivot base 622. As the clamp arm 210 pivots, the clamp pins 610 will correspondingly move downwards (vertically) within the vertical slot 612*a*. In contrast, to close the clamp arm 210, the clevis 502 may be urged (translated) in a proximal direction C (FIG. 6A). As the clevis 502 moves proximally, the clamp pins 610 will be forced against the vertical slot 612*a*, albeit in the opposite direction, which transfers the load to the pivot pin 624 and thereby urges the clamp arm 210 to pivot relative to the pivot base 622. As the clamp arm 210 pivots, the clamp pins 610 will correspondingly move upwards (vertically) within the vertical slot 612*a*.

Figure 6C:
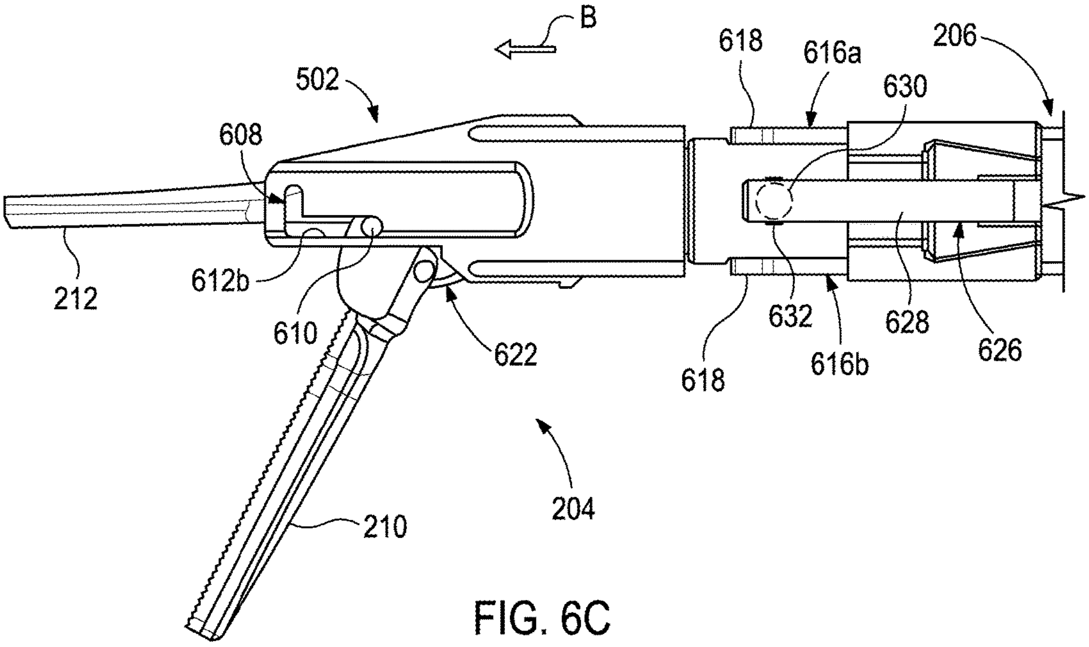

Referring now to FIGS. 6B and 6C, with continued reference to FIG. 6A, illustrated are schematic side views of the end effector 204 showing a step in example disassembly of the clamp assembly, according to one or more embodiments. To be able to disassemble the clamp assembly from proximal portions of the surgical tool 200 and, more specifically, to separate the end effector 204 from the wrist 206, the clevis 502 must first be disengaged from the distal ends of the drive members 616*a,b*. The clevis 502 may be made of a flexible material and, as best seen in FIG. 6B, the proximally extending tabs 614 may be able to be flexed radially outward, as shown by the arrows D, to disengage the coupling heads 618 from the corresponding head apertures 620 (FIG. 6A). In at least one embodiment, the tabs 614 may be manually flexed to disengage the coupling heads 618 from the head apertures 620, but a tool may alternatively be used to flex the tabs 614 radially outward D. In other embodiments, however, the coupling heads 618 may alternatively be deflected radially inwards (in a direction opposite the direction D) and out of engagement with the corresponding head aperture 620. In yet other embodiments, the coupling heads 618 may be operatively coupled to the corresponding head apertures 620 using one or more mechanical fasteners (not shown), such as one or more set screws, clips, etc., and removing or disengaging such mechanical fasteners may disengage the coupling heads 618 from the corresponding head aperture 620.

Once the coupling heads 618 are disengaged from the corresponding head apertures 620 (FIG. 6A), the clevis 502 will then be free to move in the distal direction B, as shown in FIG. 6C. As the clevis 502 moves distally B, the clamp pins 610 translate longitudinally in the corresponding longitudinal slot 612*b* of the pivot channel 608. The clevis 502 is shown in FIG. 6A in the first or "attached" position, and is shown in FIG. 6B in the second or "released" position.

Referring specifically to FIG. 6C, moving the clevis 502 distally B from the attached position to the released position exposes a retaining mechanism 626 configured to help maintain alignment of the blade 212 (both axially and radially) with the wrist 206 (FIGS. 2 and 4), and also to secure the clamp assembly (e.g., the clamp arm 210, the clevis 502, and the pivot base 622) to proximal portions of the surgical tool 200. The retaining mechanism 626 includes distally extending fingers 628 (only one shown), and a boss 630 (shown in dashed lines) may be included on each finger 628 and configured to be received within a corresponding aperture 632 (only one visible) defined by the pivot base 622. Detaching (disengaging) the boss 630 from the corresponding aperture 632 allows the pivot base 622, the clamp assembly, and the blade 212 to be detached (e.g., unscrewed) from component parts included in the drive housing 208 (FIGS. 2 and 4), as discussed below.

Figure 7A:
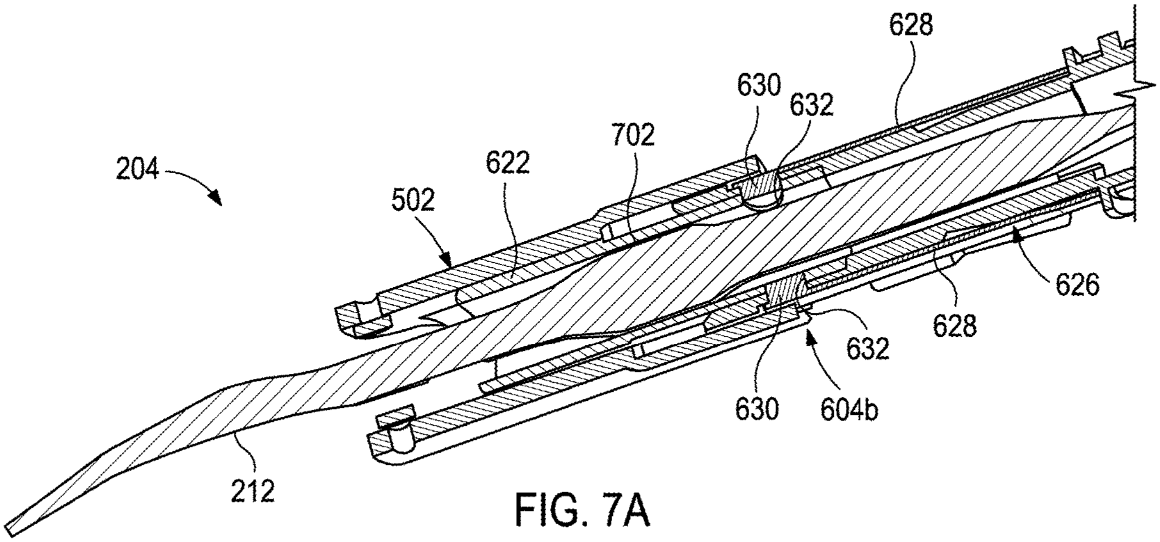
FIGS. 7A and 7B are cross-sectional isometric and side views respectively of the end effector and the clamp assembly, according to one or more embodiments.
Figure 7B:
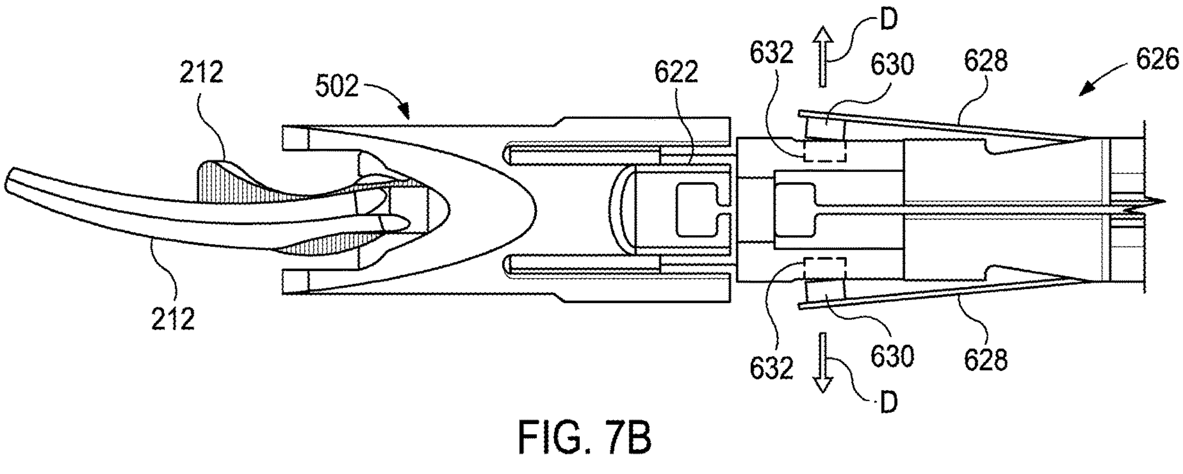

FIGS. 7A and 7B are cross-sectional isometric and side views respectively of the end effector 204 and the clamp assembly, according to one or more embodiments. Referring first to FIG. 7A, the blade 212 is shown received and extending within the pivot base 622 fixedly attached to the blade 212, such as being crimped thereto as at an enlarged portion 702 of the blade 212. In at least one embodiment, an elastomeric sleeve (not shown) may be arranged between the pivot base 622 and the blade 212. In such embodiments, the sleeve may be configured to insulate the pivot base 622 and may also provide damping and fluid isolation while helping enhance the crimped engagement between the two components. As will be appreciated by those skilled in the art, the pivot base 622 may alternatively be attached to the blade 212 in other ways such that the two components operate as a single component part.

FIG. 7A also depicts the retaining mechanism 626, which includes the distally extending fingers 628, where each finger 628 includes a corresponding boss 630 defined or otherwise provided thereon. In some embodiments, as illustrated, the bosses 630 may be arranged at the distal ends of each finger 628, but could alternatively be arranged at other locations along the length of the fingers 628. The bosses 630 are sized to be received within corresponding apertures 632 defined on angularly opposite sides of the pivot base 622. When the bosses 630 are received within the apertures 632, the clamp assembly (e.g., the clamp arm 210, the clevis 502, and the pivot base 622) and the blade 212 will be axially secured to the proximal portions of the surgical tool 200.

In the illustrated view, the clevis 502 is positioned proximally such that the proximal end 604*b* of the clevis 502 extends over the distal end of each finger 628, and more particularly over the location where the bosses 630 are received within the apertures 632. Placing the clevis 502 over this location prevents the bosses 630 from disengaging from the corresponding apertures 632 during normal operation of the device.

In FIG. 7A, the clevis 502 is shown in the attached position, and in FIG. 7B the clevis 502 is shown moved distally B to the released position, as described above with reference to FIG. 6C. As the clevis 502 moves to the released position, the distal end of the retaining mechanism 626 becomes exposed, which allows the fingers 628 to be flexed radially outward in the direction D and thereby disengage the bosses 630 from the corresponding apertures 632 (shown in dashed lines). In some embodiments, the fingers 628 may be manually flexed radially outward, but could alternatively be flexed radially outward using a tool or machine or the like. Once the bosses 630 are disengaged from the corresponding apertures 632, the clamp assembly (e.g., the clamp arm 210, the clevis 502, and the pivot base 622) and the blade 212 may be able to be removed from proximal portions of the surgical tool 200 after detaching (e.g., unscrewing) the blade 212 from component parts included in the drive housing 208 (FIGS. 2 and 4), as discussed in more detail below.

Figure 8A:
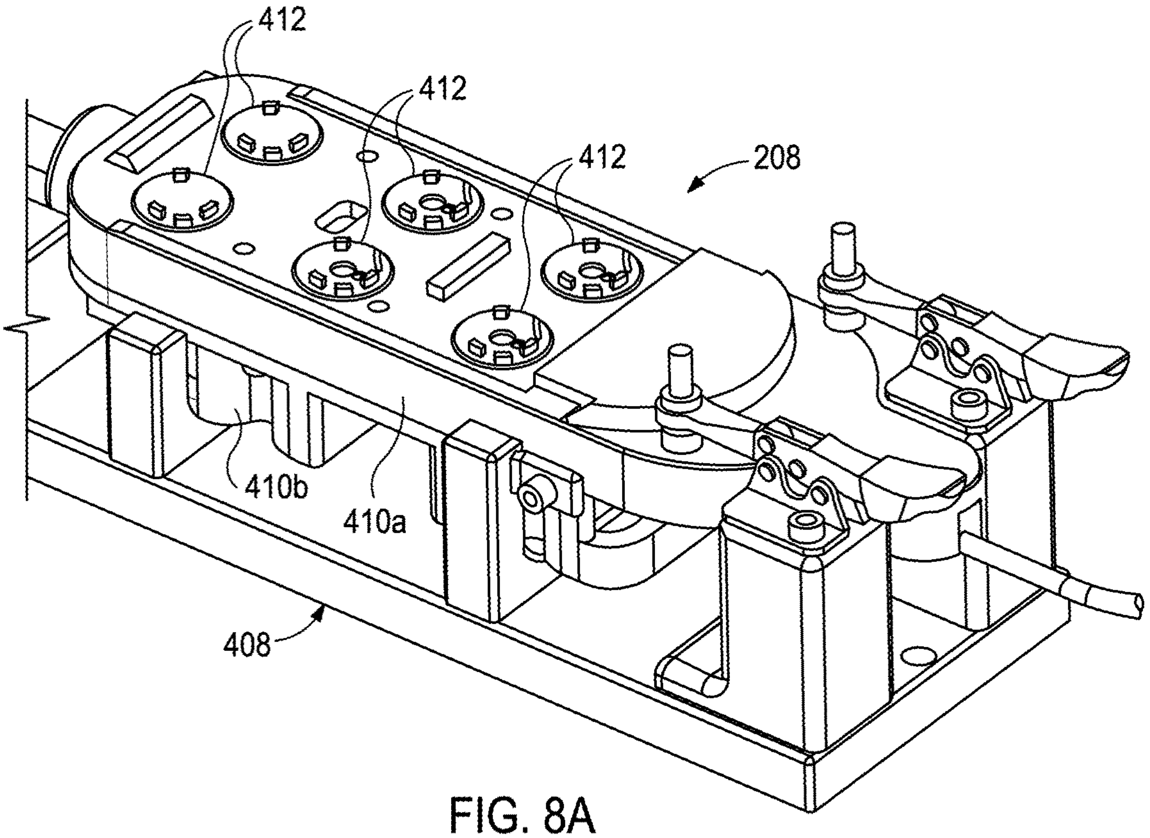
FIGS. 8A and 8B are isometric assembled and exposed views, respectively, of the drive housing mounted to the drive housing mount, according to one or more embodiments.
Figure 8B:
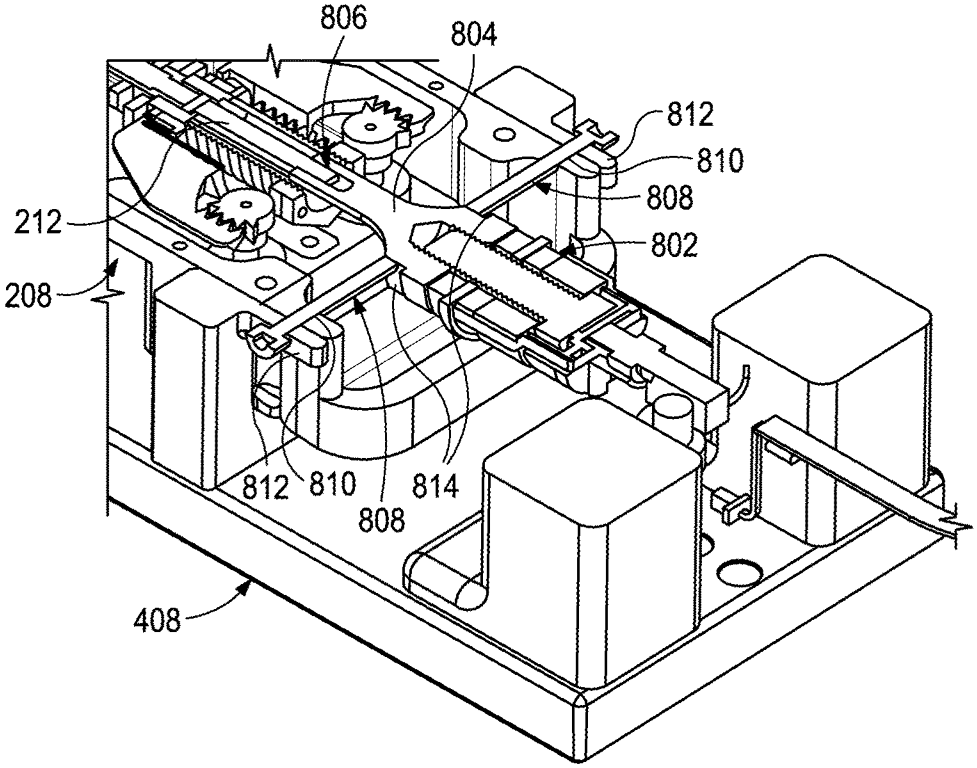

FIGS. 8A and 8B are isometric assembled and cross-sectional exposed views, respectively, of the drive housing 208 as mounted to the drive housing mount 408, according to one or more embodiments. Referring first to FIG. 8A, as indicated above, the drive housing 208 includes the bottom portion 410*a* matable with the top portion 410*b*, and one or more drive inputs 412 (six shown) may be rotatably mounted to the bottom of the drive housing 208 and rotatable (actuatable) to actuate various mechanisms of the surgical tool 200.

In FIG. 8B, the drive housing 208 houses an ultrasonic transducer 802, which includes a horn 804 arranged at a distal end of the ultrasonic transducer 802. A proximal end 806 of the blade 212 may be operatively and releasably coupled to the ultrasonic transducer 802 and, more particularly, to the horn 804. In at least one embodiment, for example, the blade 212 may be threadably attached to the horn 804, but could alternatively be releasably attached to the horn 804 in other ways, without departing from the scope of the disclosure, such as a mechanical engagement or releasable interference fit.

To be able to release the clamp assembly from proximal portions of the surgical tool 200, the blade 212 must first be detached from the ultrasonic transducer 802. To accomplish this, the ultrasonic transducer 802 may be secured against rotation within the drive housing 208. More specifically, one or more clamp screws 808 (two shown) may be extended through a side wall of the drive housing 208 via corresponding apertures 810 defined in the sidewall. In some embodiments, one or both of the apertures 810 may be threaded and the clamp screws 808 may be threadably received within the corresponding apertures 810. In other embodiments, however, the clamp screws 808 may be threadably received within portions 812 of the drive housing mount 804, without departing from the scope of the disclosure.

Once extended through the apertures 810, the clamp screws 808 may be advanced laterally into the interior the drive housing 208 until engaging the ultrasonic transducer 802. In at least one embodiment, the clamp screws 808 may be advanced until engaging the horn 804, but could alternatively be advanced until engaging other portions of the ultrasonic transducer 802, without departing from the scope of the disclosure. In some embodiments, the ultrasonic transducer 802 may provide and otherwise define opposing flat surfaces 814 engageable by the clamp screws 808 as they are advanced laterally into the drive housing 208 to engage the ultrasonic transducer 802.

Advancing the clamp screws 808 into the apertures 810 to engage the ultrasonic transducer 802 provides opposing lateral loads on opposing lateral sides of the ultrasonic transducer 802. The opposing lateral loads may be able to secure the ultrasonic transducer 802 within the drive housing 208 against rotational movement as the blade 212 is detached from the horn 804.

Once the ultrasonic transducer 802 is secured against rotation within the drive housing 208, the blade 212 may be disengaged from the ultrasonic transducer 802 (i.e., the horn 804). In embodiments where the blade 212 is threaded to the ultrasonic transducer 802 this can be accomplished by unthreading the blade 212 from the ultrasonic transducer 802. In some embodiments, as described in more detail below, this can be done by manually rotating the blade 212 relative to the ultrasonic transducer 802 and thereby unscrewing the blade 212 from the horn 804. In other embodiments, however, one or more of the drive inputs 412 (FIG. 7A) may be actuatable (rotatable) to unscrew (unthread) the blade 212 from the horn 804. This can be accomplished, for example, by securing a robotic manipulator to the bottom portion 410*a* of the drive housing 208 and mating drive outputs provided by the robotic manipulator with corresponding drive inputs 412. Once the robotic manipulator is properly secured to the drive housing 208, the robotic manipulator may be operated to rotate the corresponding drive inputs 412, which may cause the blade 212 to unscrew (unthread) from the horn 804.

Figure 9A:
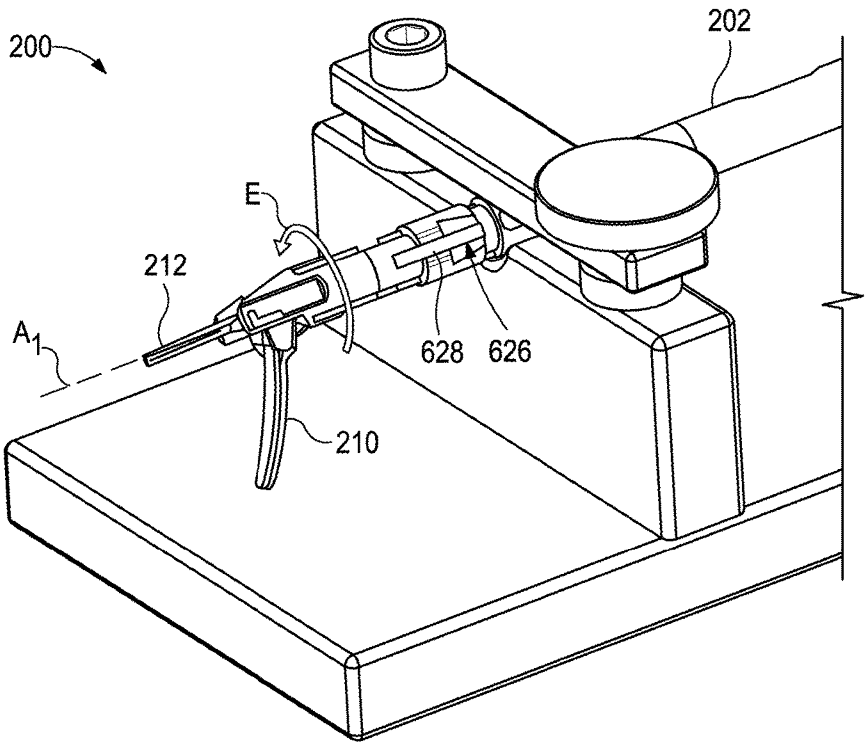
FIGS. 9A and 9B are isometric side views of the distal end of the surgical tool showing progressive disassembly of the clamp assembly from proximal portions of the surgical tool, according to one or more embodiments.
Figure 9B:
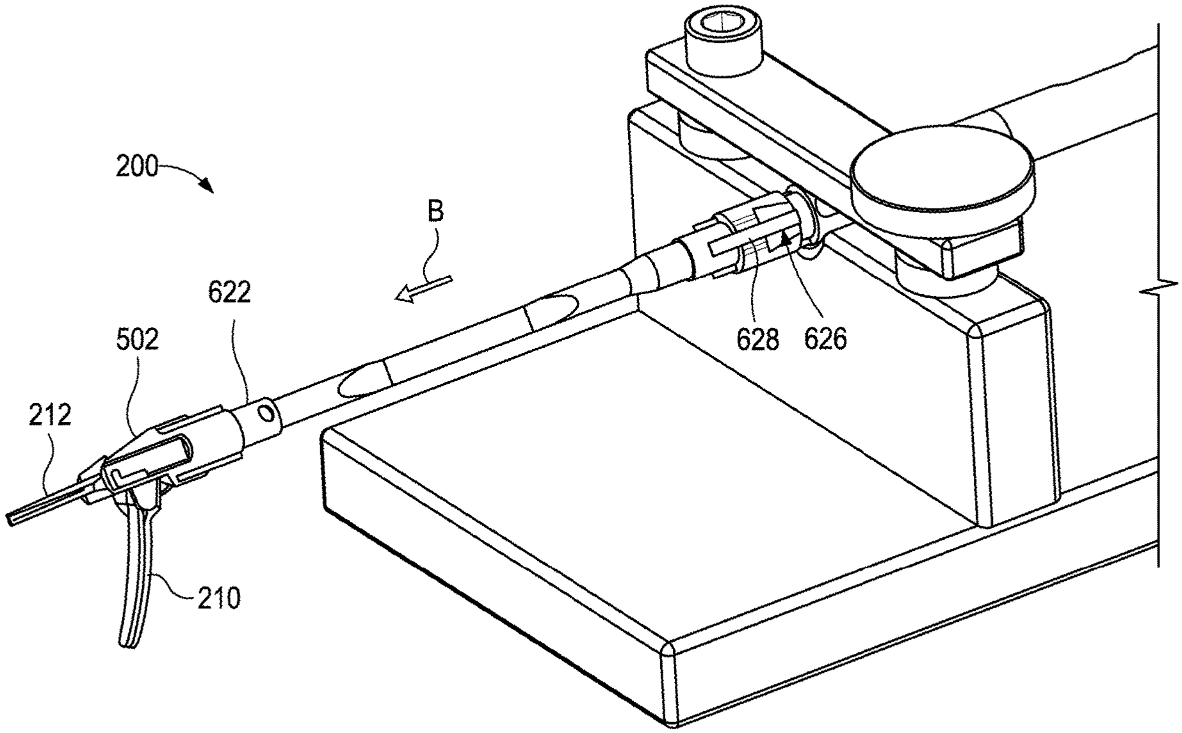

FIGS. 9A and 9B are isometric side views of the distal end of the surgical tool 200 showing progressive disassembly of the clamp assembly and the blade 212 from proximal portions of the surgical tool 200, according to one or more embodiments. To remove the blade 212 and the clamp assembly (e.g., the clamp arm 210, the clevis 502, and the pivot guide 622), the proximal end 806 (FIG. 8B) of the blade 212 must first be uncoupled (e.g., unthreaded) from the ultrasonic transducer 802 (FIG. 8B), as generally described above with reference to FIG. 8B. In embodiments where the blade 212 must be manually unthreaded from the ultrasonic transducer 802, the blade 212 and the clamp assembly may be rotated simultaneously about the longitudinal axis $A_1$ of the shaft 202 and relative to the proximal portions of the surgical tool 200, as shown by the arrow E in FIG. 9A. In some embodiments, as the blade 212 and the clamp assembly are rotated in the angular direction E, the fingers 628 of the retaining mechanism 626 may be flexed radially outward to disengage the bosses 630 (FIGS. 6C and 7A-7B) of the retaining mechanism 626 from the pivot guide 622.

In FIG. 9B, once the proximal end 806 (FIG. 8B) of the blade 212 is unthreaded from the ultrasonic transducer 802 (FIG. 8B), the blade 212 and the clamp assembly (e.g., the clamp arm 210, the clevis 502, and the pivot guide 622) may be moved distally B. Moving the blade 212 and the clamp assembly distally B will eventually detach (remove) the blade 212 and the clamp assembly from the proximal portions of the surgical tool 200. Notably, the blade 212 and the clamp assembly can be removed from proximal portions of the surgical tool while the wrist 206 (FIGS. 2, 4, and 5B) remains intact and otherwise operational. The clamp assembly may then be disassembled (detached) from the blade 212 by removing the clevis 502, detaching the clamp arm 210 from the pivot guide 622, and then removing the pivot guide 622 from the blade 212.

Portions of the end effector 204, such as the blade 212, the clamp arm 210, the clevis 502, and the pivot guide 622 may be each constitute a "consumable" that may be replaced following disassembly of the surgical tool 200, as generally described herein. An additional "consumable" may include the elastomeric sleeve that may be positioned between the pivot base 622 and the blade 212, as briefly mentioned above. Each of these components may be considered high-wear components that have a shortened lifespan, and thus may need to be replaced periodically via the presently disclosed circularity processing system and method.

Figure 10A:
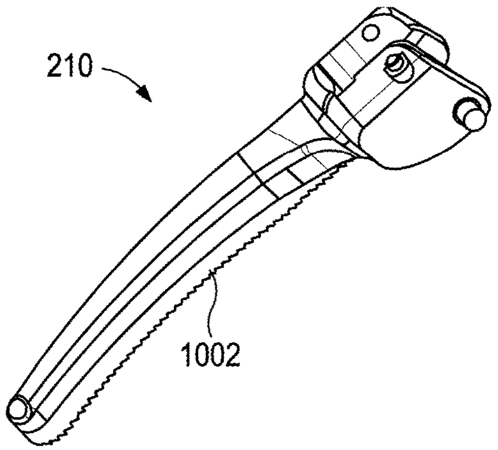
FIGS. 10A-10D are isometric side views of example consumables for the surgical tool 200, according to embodiments disclosed herein.
Figure 10B:
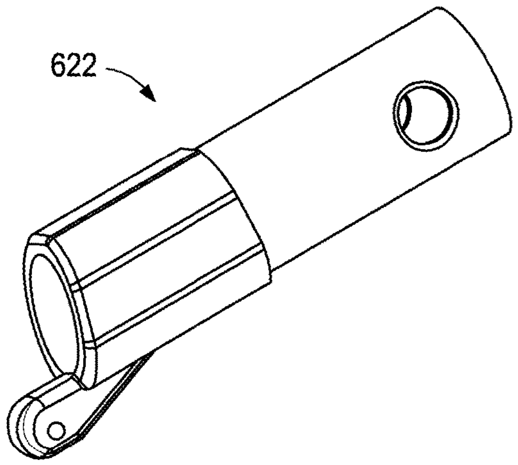
Figure 10C:
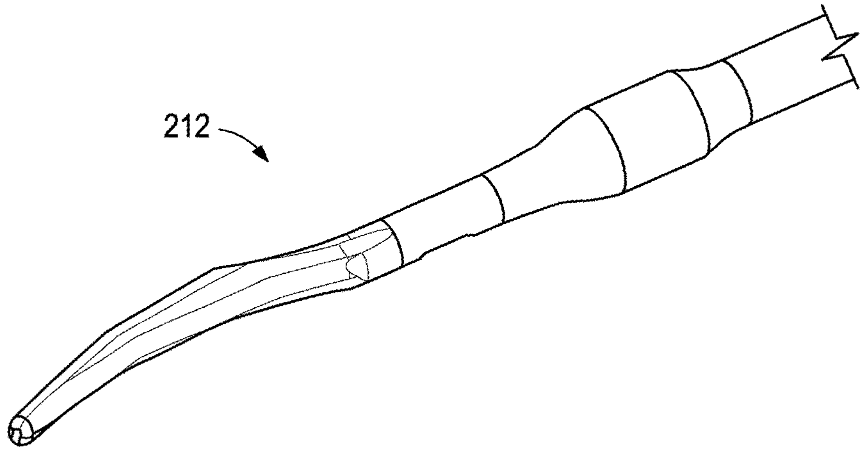
Figure 10D:
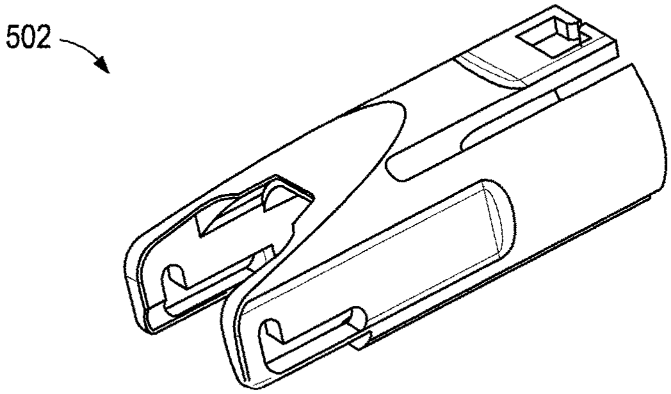

FIGS. 10A-10D are isometric side views of example consumables for the surgical tool 200, according to embodiments disclosed herein. More particularly, FIG. 10A is an isometric view of the clamp arm 210. In some embodiments, the clamp arm 210 may include a tissue pad 1002 that may be removed and replaced from the clamp arm 210, thus enabling the clamp arm 210 itself to be reused along with the clevis 502 (FIG. 10D). FIG. 10B is an isometric view of the pivot guide 622, FIG. 10C is an isometric view of the distal end of the blade 212, and FIG. 10D is an isometric view of the clevis 502. As indicated herein, the clamp arm 210, the clevis 502, and the pivot guide 622 are combined to form the clamp assembly described herein. One or more of these component parts may be replaced as a "consumable" during the circularity processing methods described herein. At the time of replacement, the pivot base 622 may be physically joined to the blade 212 (e.g., crimped), so they will not be easily separable.

The foregoing steps of disassembly and detachment of the surgical tool 200 (FIG. 2) up to this point may then be reversed to place the surgical tool 200 back into service. In particular, in a process that reverses the process outlined in FIGS. 9A-9B above, the clamp assembly may be reassembled to the blade 212. In particular, the blade 212 may be received within the pivot guide 622 and the pivot guide 622 may be secured to the outer surface of the blade 212, such as via crimping. The clamp arm 210 may then be pivotably attached to the pivot guide 622 at the pivot pin 624 (FIG. 6B). The clevis 502 may then be received over the combined blade 212 and pivot guide 622.

The blade 212 may then be inserted into the shaft 202 and advanced until the proximal end 806 (FIG. 8B) of the blade 212 enters the drive housing 208 and reaches the ultrasonic transducer 802 (FIG. 8B). In embodiments where the blade 212 is threaded to the ultrasonic transducer 802, the blade 212 and the clamp assembly may then be rotated simultaneously to thread the proximal end 806 of the blade 212 to the ultrasonic transducer 802 (FIG. 8B). In embodiments where one or more of the drive inputs 412 (FIG. 7A) are actuatable (rotatable) to screw (thread) the blade 212 to the ultrasonic transducer 802, the robotic manipulator may be operated to rotate the drive inputs 412 in the appropriate direction to thereby screw the blade 212 into the ultrasonic transducer 802.

In a process that reverses the process outlined in FIGS. 8A-8B, the clamp screws 808 may be reversed out of engagement with the ultrasonic transducer 802 and unthreaded from the drive housing 208 and/or the drive housing mount 804.

In a process that reverses the process outlined in FIGS. 7A and 7B, the bosses 630 provided on the distal ends of the distally extending fingers 628 of the retaining mechanism 626 may be received within the corresponding apertures 632 defined on angularly opposite sides of the pivot base 622. This axially secures the clamp assembly to the proximal portions of the surgical tool 200 and ensures that the blade 212 is properly aligned with the clamp arm 210.

In a process that reverses the processes outlined in FIGS. 5A-5B and 6A-6C, the clevis 502 may then be moved proximally C to enable to the coupling heads 618 provided by the drive members 616*a,b* to be received within the corresponding head apertures 620 defined in the clevis 502. This effectively couples the associated drive member 616*a,b* to the clevis 502 such that longitudinal movement of the drive member 616*a,b* correspondingly moves the clevis 502 in the same longitudinal direction (e.g., distally or proximally). This also enables coordinated movement of the drive members 616*a,b* to pivot the clamp arm 210 between the open and closed positions. Moreover, as the clevis 502 moves proximally C, the clamp pins 610 translate longitudinally in the corresponding longitudinal slot 612 of the pivot channel 608, and eventually locate the corresponding vertical slots 612*a* and translate vertically in the vertical slots 612*a*.

Finally, in a process that reverses the process outlined in FIG. 4, the surgical tool 200 may be detached and removed from the disassembly fixture 402. The surgical tool 200 may then be cleaned and tested, then delivered to a distribution center and subsequently sent to an end user (e.g., a hospital, a surgeon, an operator, etc.) to be placed in service.

Figure 11:
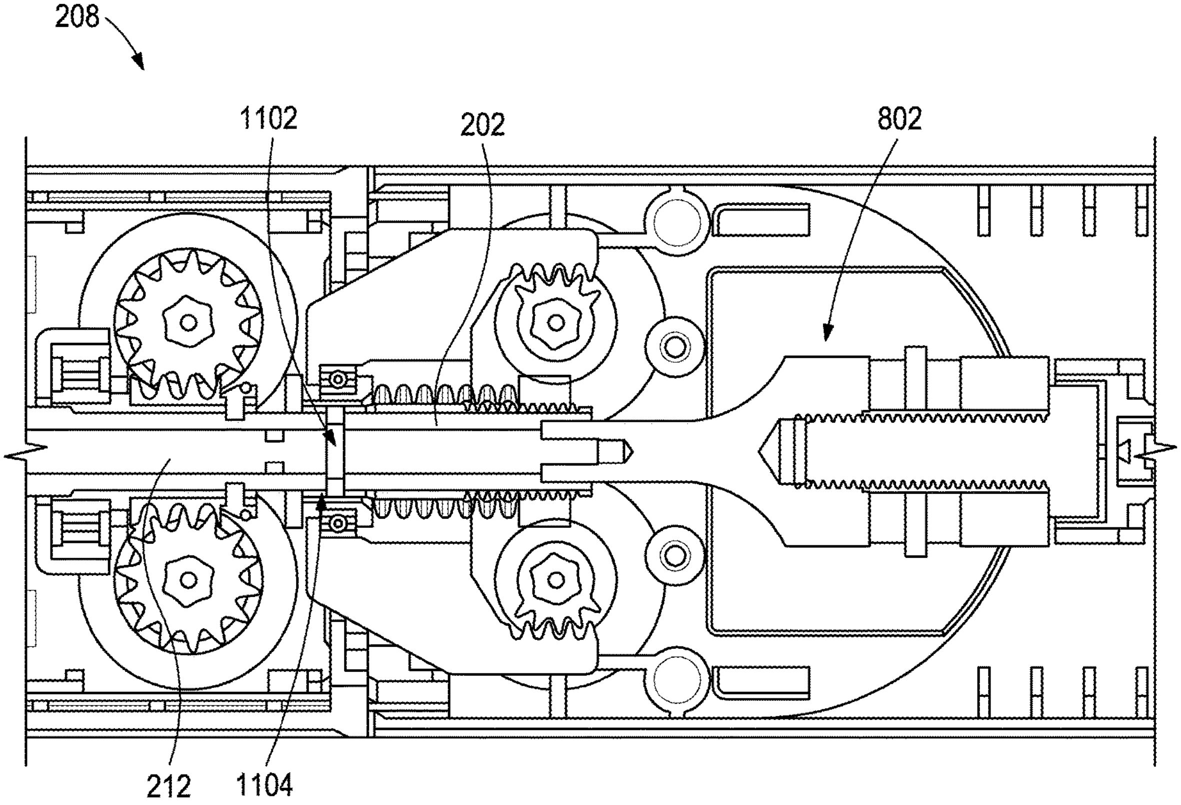
FIG. 11 is a cross-sectional, exposed view of the interior of the drive housing, according to one or more additional embodiments

FIG. 11 is a cross-sectional, exposed view of the interior of the drive housing 208, according to one or more additional embodiments. As illustrated, the blade 212 is operatively coupled to the ultrasonic transducer 802, as generally described above, and extends within the shaft 202. In some embodiments, as illustrated, the drive housing 208 may include a proximal rotational coupling component 1102 configured to couple the blade 212 to the shaft 202 such that the blade 212 will be unable to rotate relative to the shaft 202 when the proximal rotational coupling component 1102 is properly installed. In some embodiments, the proximal rotational coupling component 1102 may comprise a pin that extends through coaxially aligned portions of the shaft 202 and the blade 212.

As illustrated, the proximal rotational coupling component 1102 may be sized to be received within a slot 1104 defined in the shaft assembly that holds the shaft 202 in place. Receiving the proximal rotational coupling component 1102 within the slot 1104 may allow the blade 212 to translate relative to the shaft 202 during assembly and disassembly of the blade 212 from the ultrasonic transducer 802.

Embodiments disclosed herein include:

A. A method of replacing a consumable of a surgical tool includes securing the surgical tool, the surgical tool including a drive housing containing an ultrasonic transducer, an elongate shaft extending distally from the drive housing, an end effector arranged at a distal end of the shaft and including a blade operatively coupled to the ultrasonic transducer and extending from drive housing within the shaft, and a clamp assembly that includes a clevis extending about the blade and a clamp arm pivotably coupled to the clevis such that axial movement of the clevis causes the clamp arm to move between open and closed positions, and a wrist interposing the distal end of the shaft and the end effector. The method may further include decoupling the blade from the ultrasonic transducer, removing the end effector from the wrist and proximal portions of the surgical tool, replacing the consumable of the surgical tool, and reconnecting the end effector to the wrist and the proximal portions of the surgical tool.

B. A surgical tool configured for a circularity processing system includes a drive housing containing an ultrasonic transducer, an elongate shaft extending distally from the drive housing, an end effector arranged at a distal end of the shaft and including a blade operatively coupled to the ultrasonic transducer and extending from drive housing within the shaft, a clamp assembly that includes a clevis extending about the blade, and a clamp arm pivotably coupled to the clevis such that axial movement of the clevis causes the clamp arm to move between open and closed positions, and a pivot base interposing the blade and the clevis and defining first and second apertures on opposing sides of the pivot base. The surgical tool further including a wrist interposing the distal end of the shaft and the end effector, and a retaining mechanism including first and second distally extending fingers, each finger providing a boss receivable within a corresponding one of the first and second apertures of the pivot base, wherein the clevis is movable between an attached position, where the clevis extends over a distal end of the retaining mechanism and thereby prevents the boss from disengaging from the corresponding one of the first and second apertures, and a released position, where the clevis moves distally to expose the distal end of the retaining mechanism, and wherein, when the clevis is in the released position, the boss provided on each distally extending finger is disengageable from the corresponding one of the first and second apertures thereby allowing the end effector to be removed from proximal portions of the surgical tool.

C. A method of replacing a consumable of a surgical tool includes securing the surgical tool, the surgical tool including a drive housing including one or more drive inputs rotatably mounted thereto and containing an ultrasonic transducer, an elongate shaft extending distally from the drive housing, an end effector arranged at a distal end of the shaft and including a blade operatively coupled to the ultrasonic transducer and extending from drive housing within the shaft, and a clamp assembly that includes a clevis extending about the blade and a clamp arm pivotably coupled to the clevis such that axial movement of the clevis causes the clamp arm to move between open and closed positions, a wrist interposing the distal end of the shaft and the end effector, and securing the ultrasonic transducer within the drive housing against rotation. The method further including unthreading a proximal end of the blade from the ultrasonic transducer by rotating the one or more drive inputs, removing the end effector from the wrist and proximal portions of the surgical tool, replacing the consumable of the surgical tool, and reconnecting the end effector to the wrist and the proximal portions of the surgical tool.

Each of embodiments A, B, and C may have one or more of the following additional elements in any combination: Element 1: wherein the surgical tool further includes first and second drive members extending from the drive housing and releasably coupled to the clevis such that movement of the first and second drive members correspondingly moves the clevis to open or close the clamp arm, and wherein removing the end effector from the wrist and proximal portions of the surgical tool comprises disconnecting the clevis from the first and second drive members, the clevis providing first and second distally extending arms and a pivot channel defined in each distally extending arm, and the clamp arm providing first and second laterally extending clamp pins received within the pivot channels, and moving the clevis distally from the first and second drive members and thereby longitudinally translating the first and second clamp pins in the pivot channels. Element 2: wherein each drive member provides a coupling head and the clevis provides first and second head apertures configured to receive each coupling head, and wherein disconnecting the clevis from the first and second drive members comprises disengaging the coupling head of each drive member from the first and second head apertures. Element 3: wherein the first and second head apertures are defined in corresponding first and second proximally extending tabs, and wherein disengaging the coupling head of each drive member from the first and second head apertures comprises flexing the first and second proximally extending tabs radially outward and out of engagement with the coupling head of each drive member. Element 4: wherein each pivot channel includes a vertical slot and a horizontal slot contiguous with and extending proximally from the vertical slot, the method further comprising translating the first and second clamp pins longitudinally within the horizontal slots as the clevis moves distally from the first and second drive members. Element 5: wherein the clamp assembly further includes a pivot base interposing the blade and the clevis and defining first and second apertures on opposing sides of the pivot base, and wherein removing the end effector from proximal portions of the surgical tool is preceded by accessing a distal end of a retaining mechanism including first and second distally extending fingers, each distally extending finger providing a boss receivable within a corresponding one of the first and second apertures, and flexing the first and second distally extending fingers radially outward and thereby disengaging the boss provided on each distally extending finger from the corresponding one of the first and second apertures. Element 6: wherein accessing the distal end of the retaining mechanism comprises moving the clevis distally from an attached position, where the clevis extends over the distal end of the retaining mechanism, to a released position, where the distal end of the retaining mechanism is exposed. Element 7: wherein the consumable is selected from the group consisting of the blade, the clamp arm, the clevis, and the pivot guide. Element 8: wherein decoupling the blade from the ultrasonic transducer comprises securing the ultrasonic transducer within the drive housing against rotation, and unthreading a proximal end of the blade from the ultrasonic transducer. Element 9: wherein securing the ultrasonic transducer within the drive housing against rotation comprises extending one or more clamp screws through a side wall of the drive housing, and engaging opposing sides of the ultrasonic transducer with the one or more clamp screws. Element 10: wherein unthreading the proximal end of the ultrasonic transducer from the ultrasonic transducer comprises manually rotating the blade and the clamp assembly relative to the ultrasonic transducer. Element 11: wherein the drive housing includes one or more drive inputs rotatably mounted thereto, and wherein unthreading the proximal end of the ultrasonic transducer from the ultrasonic transducer comprises attaching a robotic manipulator to the drive housing, and operating the robotic manipulator to rotate the one or more drive inputs and thereby cause the blade to unthread from the ultrasonic transducer. Element 12: wherein reconnecting the end effector to the wrist and the proximal portions of the surgical tool comprises coupling a proximal end of the blade to the ultrasonic transducer, and reconnecting the first and second drive members to the clevis. Element 13: wherein securing the surgical tool comprises mounting the surgical tool to a disassembly fixture, which includes the steps of mounting the drive housing to a drive housing mount of the disassembly fixture, and securing the end effector to an end effector mount of the disassembly fixture.

Element 14: wherein engaging the boss provided on each distally extending finger with the corresponding one of the first and second apertures axially and radially aligns the blade with the wrist. Element 15: further comprising first and second drive members extending from the drive housing and releasably coupled to the clevis such that movement of the first and second drive members correspondingly moves the clevis to open or close the clamp arm, wherein the clevis is flexible radially outward to disengage the clevis from the first and second drive members. Element 16: wherein the clevis provides first and second distally extending arms and a pivot channel is defined in each distally extending arm, the clamp arm provides first and second laterally extending clamp pins received within the pivot channels, and wherein each pivot channel includes a vertical slot and a horizontal slot contiguous with and extending proximally from the vertical slot. Element 17: wherein a proximal end of the blade is threaded to the ultrasonic transducer.

By way of non-limiting example, exemplary combinations applicable to A, B, and C include: Element 1 with Element 2; Element 2 with Element 3; Element 1 with Element 4; Element 5 with Element 6; Element 5 with Element 7; Element 8 with Element 9; Element 8 with Element 10; and Element 8 with Element 11.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The use of directional terms such as above, below, upper, lower, upward, downward, left, right, uphole, downhole and the like are used in relation to the illustrative embodiments as they are depicted in the figures, the upward direction being toward the top of the corresponding figure and the downward direction being toward the bottom of the corresponding figure.

What is claimed is:

1. A method of replacing a consumable of a surgical tool that includes:

a drive housing containing an ultrasonic transducer;

an elongate shaft extending distally from the drive housing;

an end effector arranged at a distal end of the shaft and including a blade operatively coupled to the ultrasonic transducer and extending from drive housing within the shaft, and a clamp assembly that includes a clevis extending about the blade and a clamp arm pivotably coupled to the clevis such that axial movement of the clevis causes the clamp arm to move between open and closed positions; and a wrist interposing the distal end of the shaft and the end effector, wherein the method comprises:

decoupling the blade from the ultrasonic transducer;

removing the end effector from the wrist and proximal portions of the surgical tool; and replacing the consumable of the surgical tool;

wherein the surgical tool further includes first and second drive members extending from the drive housing and releasably coupled to the clevis such that movement of the first and second drive members correspondingly moves the clevis to open or close the clamp arm, and wherein removing the end effector from the wrist and proximal portions of the surgical tool comprises:

disconnecting the clevis from the first and second drive members, the clevis providing first and second distally extending arms and a pivot channel defined in each distally extending arm, and the clamp arm providing first and second laterally extending clamp pins received within the pivot channels; and moving the clevis distally from the first and second drive members and thereby longitudinally translating the first and second clamp pins in the pivot channels.

2. The method of claim 1, wherein each drive member provides a coupling head and the clevis provides first and second head apertures configured to receive each coupling head, and wherein disconnecting the clevis from the first and second drive members comprises disengaging the coupling head of each drive member from the first and second head apertures.

3. The method of claim 2, wherein the first and second head apertures are defined in corresponding first and second proximally extending tabs, and wherein disengaging the coupling head of each drive member from the first and second head apertures comprises flexing the first and second proximally extending tabs radially outward and out of engagement with the coupling head of each drive member.

4. The method of claim 1, wherein each pivot channel includes a vertical slot and a horizontal slot contiguous with and extending proximally from the vertical slot, the method further comprising translating the first and second clamp pins longitudinally within the horizontal slots as the clevis moves distally from the first and second drive members.

5. A method of replacing a consumable of a surgical tool that includes:
  a drive housing containing an ultrasonic transducer;
  an elongate shaft extending distally from the drive housing;
  an end effector arranged at a distal end of the shaft and including a blade operatively coupled to the ultrasonic transducer and extending from drive housing within the shaft, and a clamp assembly that includes a clevis extending about the blade and a clamp arm pivotably coupled to the clevis such that axial movement of the clevis causes the clamp arm to move between open and closed positions; and
  a wrist interposing the distal end of the shaft and the end effector,
  wherein the method comprises:
  decoupling the blade from the ultrasonic transducer;
  removing the end effector from the wrist and proximal portions of the surgical tool; and
  replacing the consumable of the surgical tool;
  wherein the clamp assembly further includes a pivot base interposing the blade and the clevis and defining first and second apertures on opposing sides of the pivot base, and wherein removing the end effector from proximal portions of the surgical tool is preceded by:
  accessing a distal end of a retaining mechanism including first and second distally extending fingers, each distally extending finger providing a boss receivable within a corresponding one of the first and second apertures; and
  flexing the first and second distally extending fingers radially outward and thereby disengaging the boss provided on each distally extending finger from the corresponding one of the first and second apertures.

6. The method of claim 5, wherein accessing the distal end of the retaining mechanism comprises moving the clevis distally from an attached position, where the clevis extends over the distal end of the retaining mechanism, to a released position, where the distal end of the retaining mechanism is exposed.

7. The method of claim 5, wherein the consumable is selected from the group consisting of the blade, the clamp arm, the clevis, and the pivot guide.

8. A method of replacing a consumable of a surgical tool that includes:
  a drive housing containing an ultrasonic transducer;
  an elongate shaft extending distally from the drive housing;
  an end effector arranged at a distal end of the shaft and including a blade operatively coupled to the ultrasonic transducer and extending from drive housing within the shaft, and a clamp assembly that includes a clevis extending about the blade and a clamp arm pivotably coupled to the clevis such that axial movement of the clevis causes the clamp arm to move between open and closed positions; and
  a wrist interposing the distal end of the shaft and the end effector,
  wherein the method comprises:
  decoupling the blade from the ultrasonic transducer;
  removing the end effector from the wrist and proximal portions of the surgical tool; and
  replacing the consumable of the surgical tool;
  wherein decoupling the blade from the ultrasonic transducer comprises:
  securing the ultrasonic transducer within the drive housing against rotation; and
  unthreading a proximal end of the blade from the ultrasonic transducer.

9. The method of claim 8, wherein securing the ultrasonic transducer within the drive housing against rotation comprises:
  extending one or more clamp screws through a side wall of the drive housing; and
  engaging opposing sides of the ultrasonic transducer with the one or more clamp screws.

10. The method of claim 8, wherein unthreading the proximal end of the ultrasonic transducer from the ultrasonic transducer comprises manually rotating the blade and the clamp assembly relative to the ultrasonic transducer.

11. The method of claim 8, wherein the drive housing includes one or more drive inputs rotatably mounted thereto, and wherein unthreading the proximal end of the ultrasonic transducer from the ultrasonic transducer comprises:
  attaching a robotic manipulator to the drive housing; and
  operating the robotic manipulator to rotate the one or more drive inputs and thereby cause the blade to unthread from the ultrasonic transducer.

12. The method of claim 8, further comprising reconnecting the end effector to the wrist and the proximal portions of the surgical tool by:
  coupling a proximal end of the blade to the ultrasonic transducer; and
  reconnecting the first and second drive members to the clevis.

13. A method of replacing a consumable of a surgical tool that includes:
  a drive housing containing an ultrasonic transducer;
  an elongate shaft extending distally from the drive housing;
  an end effector arranged at a distal end of the shaft and including a blade operatively coupled to the ultrasonic transducer and extending from drive housing within the shaft, and a clamp assembly that includes a clevis extending about the blade and a clamp arm pivotably coupled to the clevis such that axial movement of the clevis causes the clamp arm to move between open and closed positions; and
  a wrist interposing the distal end of the shaft and the end effector,
  wherein the method comprises:
  decoupling the blade from the ultrasonic transducer;
  removing the end effector from the wrist and proximal portions of the surgical tool; and
  replacing the consumable of the surgical tool;
  mounting the drive housing to a drive housing mount of a disassembly fixture; and
  securing the end effector to an end effector mount of the disassembly fixture.

14. A surgical tool configured for a circularity processing system, comprising:
  a drive housing containing an ultrasonic transducer;
  an elongate shaft extending distally from the drive housing;
  an end effector arranged at a distal end of the shaft and including:
    a blade operatively coupled to the ultrasonic transducer and extending from drive housing within the shaft;

a clamp assembly that includes a clevis extending about the blade, and a clamp arm pivotably coupled to the clevis such that axial movement of the clevis causes the clamp arm to move between open and closed positions; and a pivot base interposing the blade and the clevis and defining first and second apertures on opposing sides of the pivot base;

a wrist interposing the distal end of the shaft and the end effector; and a retaining mechanism including first and second distally extending fingers, each finger providing a boss receivable within a corresponding one of the first and second apertures of the pivot base, wherein the clevis is movable between an attached position, where the clevis extends over a distal end of the retaining mechanism and thereby prevents the boss from disengaging from the corresponding one of the first and second apertures, and a released position, where the clevis moves distally to expose the distal end of the retaining mechanism, and wherein, when the clevis is in the released position, the boss provided on each distally extending finger is disengageable from the corresponding one of the first and second apertures thereby allowing the end effector to be removed from proximal portions of the surgical tool.

15. The surgical tool of claim 14, wherein engaging the boss provided on each distally extending finger with the corresponding one of the first and second apertures axially and radially aligns the blade with the wrist.

16. The surgical tool of claim 14, further comprising first and second drive members extending from the drive housing and releasably coupled to the clevis such that movement of the first and second drive members correspondingly moves the clevis to open or close the clamp arm, wherein the clevis is flexible radially outward to disengage the clevis from the first and second drive members.

17. The surgical tool of claim 14, wherein the clevis provides first and second distally extending arms and a pivot channel is defined in each distally extending arm, the clamp arm provides first and second laterally extending clamp pins received within the pivot channels, and wherein each pivot channel includes a vertical slot and a horizontal slot contiguous with and extending proximally from the vertical slot.

18. The surgical tool of claim 14, wherein a proximal end of the blade is threaded to the ultrasonic transducer.

19. A method of replacing a consumable of a surgical tool that includes:

a drive housing including one or more drive inputs rotatably mounted thereto and containing an ultrasonic transducer;

an elongate shaft extending distally from the drive housing;

an end effector arranged at a distal end of the shaft and including a blade operatively coupled to the ultrasonic transducer and extending from drive housing within the shaft, and a clamp assembly that includes a clevis extending about the blade and a clamp arm pivotably coupled to the clevis such that axial movement of the clevis causes the clamp arm to move between open and closed positions; and a wrist interposing the distal end of the shaft and the end effector, wherein the method comprises:

securing the ultrasonic transducer within the drive housing against rotation;

unthreading a proximal end of the blade from the ultrasonic transducer by rotating the one or more drive inputs;

removing the end effector from the wrist and proximal portions of the surgical tool; and replacing the consumable of the surgical tool.

* * * * *